United States Patent [19]

Hansen

[11] 4,235,963

[45] Nov. 25, 1980

[54] SAMPLING AND IDENTIFYING APPARATUS AND METHOD

[76] Inventor: Joe C. Hansen, Cromwell La., Blackfoot, Id. 83221

[21] Appl. No.: 38,273

[22] Filed: May 11, 1979

[51] Int. Cl.³ .................................................. C12Q 1/24
[52] U.S. Cl. ........................................ 435/30; 435/294; 435/295; 435/810
[58] Field of Search ...................... 435/30, 29, 31, 32, 435/33, 34, 36, 37, 38, 39, 40, 292, 293, 294, 295, 296, 299, 300, 301, 810

[56] References Cited

U.S. PATENT DOCUMENTS

| | | | |
|---|---|---|---|
| 3,205,151 | 9/1965 | Landau et al. | 435/30 X |
| 3,308,039 | 3/1967 | Nelson | 435/295 |
| 3,563,859 | 2/1971 | Fink | 435/294 |
| 3,784,448 | 1/1974 | Cekoric, Jr. et al. | 435/294 X |
| 3,907,647 | 9/1975 | Sanderson | 435/294 |
| 4,136,680 | 1/1979 | Southworth | 435/295 X |

*Primary Examiner*—Robert J. Warden
*Attorney, Agent, or Firm*—Wegner, Stellman, McCord, Wood & Dalton

[57] ABSTRACT

A disposable apparatus is provided for sampling and identifying microorganisms. In one application of the apparatus, a throat culture is taken and pathogenic microorganisms in the culture are identified. The apparatus includes a housing having a retractable strip with a streaker or inoculating pad on the distal end thereof. An identification bar having a plurality of open-faced troughs is clamped to the housing with the open faces of the troughs in line with the streaker pad on the sampling strip. A different testing media is provided in each trough. A cap encloses the end of the housing and the streaker pad. With the cap removed, the streaker pad is swabbed over the infected area after which the strip and inoculating pad are retracted to draw the pad into the housing and over the testing media in the open-faced troughs. The strip is broken off leaving the inoculating pad in the housing. The cap is reassembled on the end of the housing. The apparatus is stored at an appropriate incubation temperature for a predetermined period of time after which the cap and the clamps are removed to release the identification bar whereupon the appropriate visual inspection and diagnosis is made of the colony or colonies that have grown on the various test media.

10 Claims, 5 Drawing Figures

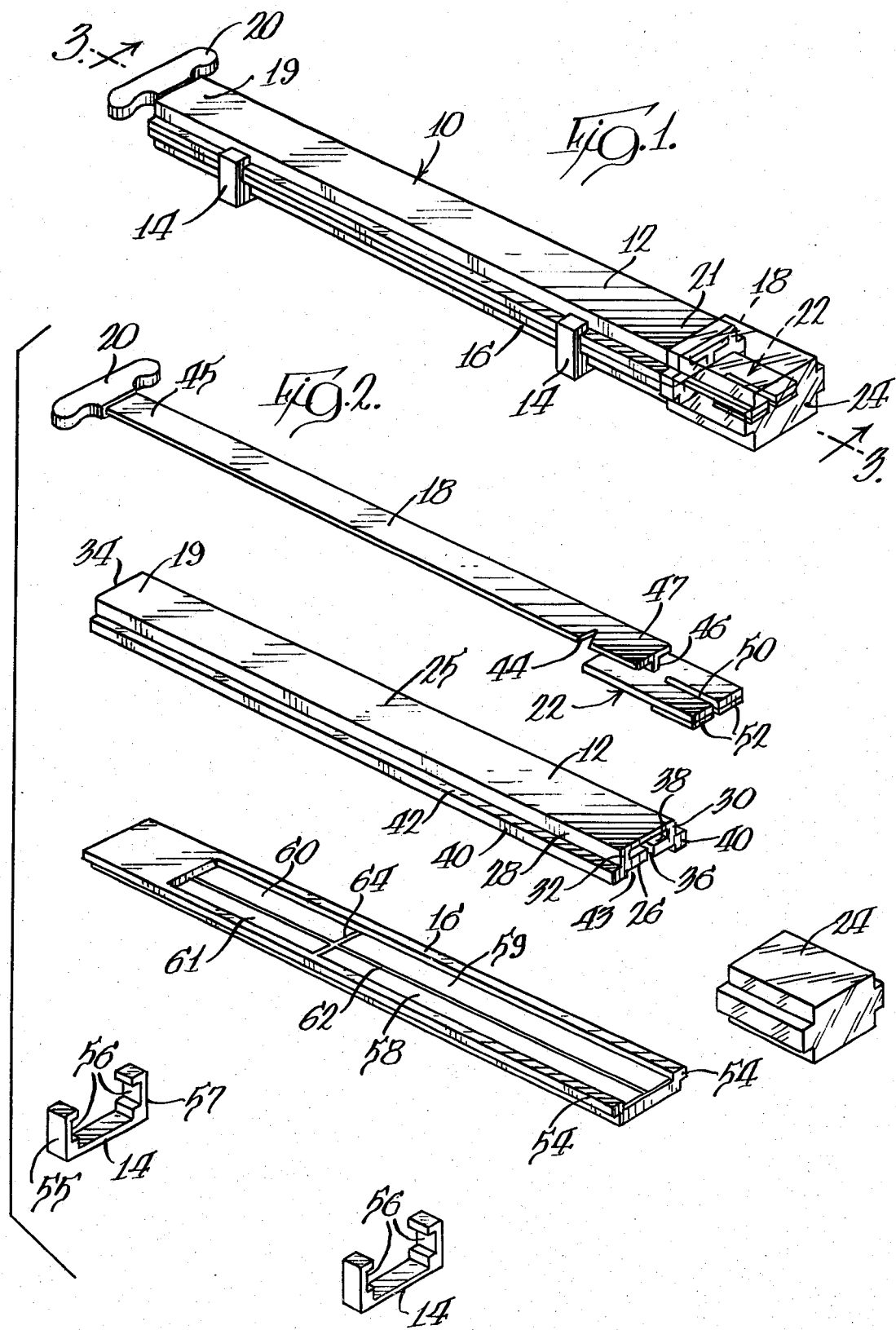

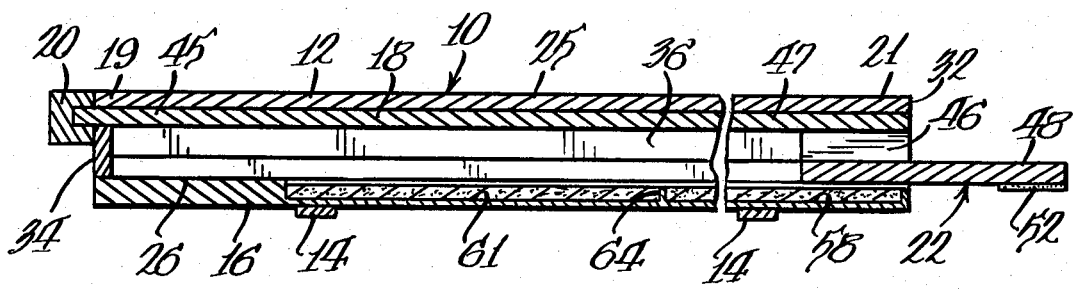
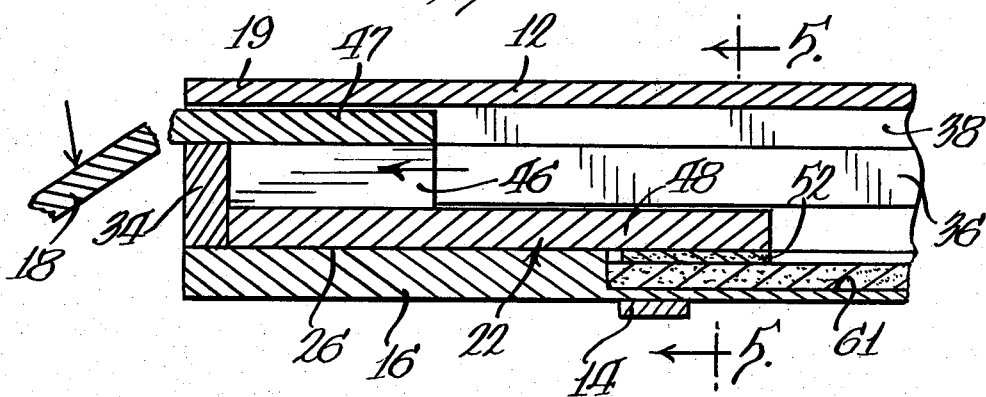
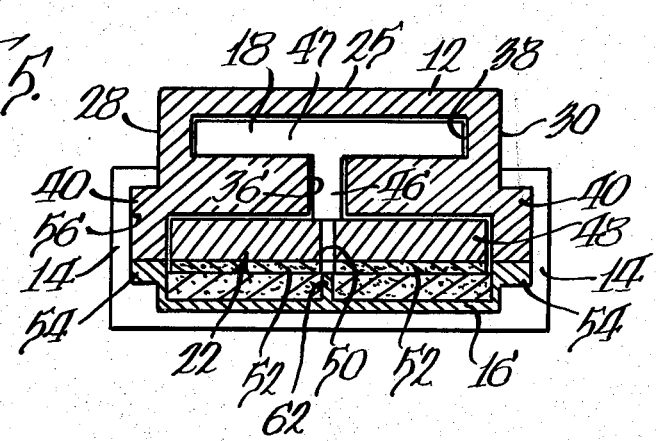

SAMPLING AND IDENTIFYING APPARATUS AND METHOD

BACKGROUND OF THE INVENTION

1. Field of the Invention

This invention relates to sampling and identifying apparatus and, more particularly, to such apparatus for sampling and identifying microorganisms.

2. Description of the Prior Art

Heretofore, pathogenic microorganisms in the throat of a patient have been found and identified in a laborious and time-consuming manner. That is, a patient's tongue is depressed by a tongue depressor stick whereupon a swab is inserted into the mouth and the area appearing infected is swabbed. The swab is placed into some type of transport media to be taken to a microbiological laboratory whereupon the swab is streaked upon blood agar. On the blood agar, a laboratory technologist or microbiologist places a disc containing an antibiotic called bacitracin which inhibits the growth of Beta-hemolytic Streptococcus group A which can be the cause of Strep throat, Rhuematic fever and, in some cases, glomerulonephritis. The sample is incubated for twenty-four hours whereupon, if there are hemolytic colonies, i.e. clear zones inside the inoculated blood agar, these would be identified as Beta-hemolytic Streptococcus group A if they were inhibited from growing by the bacitracin disc. If, however, the hemolytic colonies did not appear to be close enough to the bacitracin disc, the hemolytic colony or colonies would have to be reinoculated onto another blood agar media and the procedure with the bacitracin disc started all over again.

On the other hand, if there were hemolytic colonies not inhibited by the disc, but growing in close proximity to it, the microbiologist would then have to identify the organisms as either (A) another group of Streptococci (not inhibited by bacitracin, not grown on mannitol salt agar, not positive when grown on bile esculin agar), or (B) Staphlococcus (not inhibited by bacitracin, will grow on mannitol salt agar, and not positive when grown or tempted to be grown on bile esculin agar), or (C) Enterococcus (not inhibited by bacitracin, will not grow on 6.5% mannitol salt agar, but positive when grown on bile esculin agar).

All of the above is very time consuming, exposes the analyst to infection and, due to the manner of obtaining the culture on the initial swab, which may touch other portions of the mouth or which may pick up other infectious organisms during transport to the laboratory, produces possibly inaccurate results.

In U.S. Pat. No. 3,205,151 to W. L. Landau et al, entitled "Inoculation Device and Method", a stack of containers, each containing a test medium, are aligned with each other and an inoculating needle is initially threaded through all of the containers and test media with the point projecting beyond the end of the stack. The point of the inoculating needle is dipped into a colony which has already been isolated onto a solid media. The inoculating needle is drawn through the stack of containers to leave a trace of the colony in each container whereupon the colony is identified by growth characteristics in the different test media in the stack of containers. The Landau et al device could not be used to obtain a sample from an infected area of a patient's throat and could not be used to show the presence of specific organisms among the many that are present. Cross contamination would make these stacked containers produce inaccurate reactions. The Landau et al device requires that the swab sample be initially streaked on solid media and the colonies grown through incubation for twenty-four hours. The Landau et al device is then used to further identify a specific colony within the multiplicity of colonies. The incubation period prior to use of the Landau et al device takes up to twenty-four hours, during which time the nature of the patient's infection remains undiagnosed. The Landau et al device further provides that the inoculating needle be disposed of after it has been used to draw the colony through the stack of containers. The inoculating needle can form a source of infection to the persons using the apparatus.

SUMMARY OF THE INVENTION

An apparatus is provided for analyzing and identifying microorganisms in as fast a period of time as possible with a relatively high degree of accuracy resulting therefrom. A housing encompasses a retractable streaker strip which has attached thereto a projecting inoculating pad. The streaker strip has a weakened portion near the inoculating pad whereby the strip may be broken off, thereby leaving the inoculating pad in the housing and not available for contaminating the surrounding surfaces or individuals. An identification bar is clamped to one side of the housing and has a plurality of open-faced troughs in which different test media are provided. The open faces of the troughs are aligned with the surface of the inoculating pad so that as the streaker strip is retracted into the housing, the inoculating pad will be drawn across the surfaces of the test media. A cap encompasses the inoculating pad and one end of the housing and identification bar to seal the apparatus from the atmosphere.

In use, the cap is removed and the distal end of the apparatus is inserted in the mouth of a patient so that the inoculating pad can be swabbed across the infected area. The streaker strip is immediately retracted to draw the inoculating pad into the housing. The apparatus is now removed from the patient's mouth and the strip draws the inoculating pad slowly across the surface of the open-faced troughs in the identification bar. When the strip is completely retracted, the strip is broken off and the cap is reassembled on the open end of the housing. The apparatus is now incubated for a twenty-four hour period at a preselected temperature after which time the identification bar can be removed from the apparatus and examined by a microbiologist, or the like.

The microbiologist can identify the different colonies and the nature of the infection by the various reactions exhibited on each of the open troughs of the identification bar.

The apparatus eliminates the need for a tongue depressor which may act as a source of infection for others after it is disposed of, eliminates the swab which normally would be disposed of and which could form a source of contamination, eliminates the transport media that was necessary to transport the swab to the appropriate area for examination and brings into one piece of apparatus all of the testing media needed for identification of the particular types of infection sought to be identified.

BRIEF DESCRIPTION OF THE DRAWINGS

The details of construction and operation of the invention are more fully described with reference to the accompanying drawings which form a part hereof and in which like reference numerals refer to like parts throughout.

In the drawings:

FIG. 1 is a perspective view of a preferred form of my invention;

FIG. 2 is an exploded perspective view of the embodiment of FIG. 1;

FIG. 3 is a cross-sectional view taken along the line 3—3 of FIG. 1;

FIG. 4 is an enlarged partial sectional view similar to FIG. 3 with the streaker strip retracted; and, FIG. 5 is a cross-sectional view taken along the line 5—5 of FIG. 4.

DESCRIPTION OF THE PREFERRED EMBODIMENT

Referring to the drawings, and in particular FIGS. 1 and 2, a sampling and identifying apparatus 10 is illustrated and includes an elongate housing 12 to which is clamped, by means of clamps 14, an identification bar 16. A retractable streaker strip or rod 18 is disposed in the housing 12 and has a handle 20 which projects outwardly from the proximal end 19 of the housing 12 and has an inoculator 22 projecting from the distal end 21 of the housing 12. A cap 24 fits over the inoculator 22 and engages with both the distal end 21 of the housing 12 and the distal end of the identification bar 16. The apparatus 10 is initially supplied in a bag, not shown, for maintaining the apparatus in a sterile condition prior to use.

Referring more in detail to the construction of the various elements of the apparatus, I have shown in FIGS. 2 through 5 the details of the construction. The housing 12 is an elongate body member having a top wall 25, a slotted bottom wall 26, oppositely facing side walls 28 and 30, and end walls 32 and 34. The bottom wall 26 has a lengthwise elongate slot 36 running the full length thereof which permits communication with a cavity 38 running the full length of the housing 12. A pair of clamping flanges 40 extend outwardly from each side wall 28,30 to provide a shoulder 42 facing upwardly from the flanges 40. The flanges 40 project downwardly beyond the plane of the bottom wall 26 so as to provide an elongate slot 43 between the overhanging portions of the flanges 40. The slot 43 serves as a guide track for the inoculator 22.

The streaker strip or rod 18 is elongate and has a width and depth substantially coinciding with the width and depth of the cavity 38 in the housing 12 so that it can be freely slidable therein. The handle grip 20 is secured to the proximal end 45 of the streaker strip 18 and is shaped for ready gripping by an operator when the strip is to be manipulated. A notch 44 or similar weakening system is provided near the distal end 47 of the strip 18 so as to weaken the strip, making it possible to readily sever the strip at or in the vicinity of the notch 44.

Downwardly depending from the midportion of the strip 18 at the distal end 47 thereof is a web 46 which extends along the axis of the strip 18 part of the distance to the notch 44. The inoculator 22 is attached to the web 46 and includes a rectangular streaker plate 48 which is disposed substantially parallel to the plane of the strip 18 and is spaced downwardly therefrom. The streaker plate 48 extends distally beyond the end of the strip 18 and has a slot 50 cut in from the leading edge thereof to divide part of the plate into two halves. Cotton or felt pads 52 are secured to the bottom faces of the two halves of the streaker plate 48 so as to be laterally disposed to one another and so as to project beyond the plane of the streaker plate. As shown in FIGS. 3, 4 and 5, streaker strip 18 is disposed in the cavity 38 with the web 46 extending through the slot 36 so as to dispose the streaker plate 48 in the recess 43 and in contact with the bottom wall 26 of the housing 12. The distance from the proximal end 45 of the streaker strip 18 to the distal end 47 of the streaker strip 18 substantially coincides with the length of the housing 12 so that the handle 20 extends outwardly from the end 34 of the housing 12 with the pads 52 and a portion of the streaker plate 48 extending distally from the other end 30 of the housing 12.

The identification bar 16 is an elongate flat member having sidewardly extending flanges 54 with the upper faces of the flanges 54 being adapted to be held in contact with the bottom faces of the flanges 40 on the housing 12. When the identification bar 16 is so assembled with the flanges 54 mating with the flanges 40 on the housing 12, the specially shaped clamps 14, which have indents 56 in the spaced legs 55,57, are sized to embrace the mating flanges 40 and 54 and to hold the identification bar 16 assembled on the housing 12.

The identification bar 16 has at least one open-faced trough 58 formed in the top surface thereof. In the preferred illustrated embodiment, there are four open-faced troughs 58, 59, 60, 61 which are separated by upstanding ribs 62,64 which extend at right angles to each other so as to define recessed areas into which testing media can be located.

With the identification bar 16 assembled to the slotted wall 26 of the housing 12 by means of the clamps 14, and with the streaker strip 18 nested in the cavity 38 in the housing 12, the streaker plate 48 will extend distally from the housing 12 with the cotton or felt inoculating pads 52 extending downwardly therefrom. The exposed surfaces of the pads 52 project downwardly an amount sufficient to permit the pads to contact and move across the surfaces of the testing media located in the open-faced troughs 58, 59, 60, 61 when the streaker strip 18 is drawn through the housing 12.

The end cap 24 has a blind cavity therein shaped to substantially conform with the peripherial shape of the housing 12 and identification bar 16 when said housing 12 and bar 16 are clamped together. The axial extent of the protective cap 24 is sufficient to enclose the extended streaker plate 48 and, in particular, that portion of the streaker plate 48 having the inoculating pads 52 thereon. The cap 24 will encompass the streaker plate 48 and inoculating pads 52 without contacting the plate 48 or the pads 52 and will telescope over the distal end 21 of the housing 12 and identification bar 16 and may be wedged thereon so as to form a seal between the housing 12 and the cap 24.

Each of the open-faced troughs 58, 59, 60, 61 is filled with a solid testing media prior to clamping the identification bar 16 to the housing 12. The assembled housing 12, identification bar 16 and protective cap 24 may be sterilized and stored in a plastic bag, or the like, for shipment. When it is desired to take a sample for test purposes, the bag and the cap 24 are removed and the patient is asked to open his mouth and look upward into the air. The apparatus 10 is inserted in the mouth of the patient so that the inoculating pads 52 on the streaker plate 48 are swabbed over the infected area. The handle 20 is pulled to retract the streaker strip 18, streaker plate 48 and pads 52 into the housing 12. The apparatus 10 is removed from the patient's mouth as the streaker strip 18 is retracted further into the housing 12. As the strip 18 is retracted, the inoculating pads 52 are drawn across the exposed surface of the test media in the four open-faced troughs 58, 59, 60, 61. When the streaker plate 48 has abutted against the inside of the end wall 34 of the housing 12, the notch 44 of the streaker strip 18 will be exposed externally of the housing 12. A slight bending of the streaker strip 18 will snap the streaker strip in line with the notch 44 whereupon the inoculating handle 20 and streaker strip 18 can be discarded. It should be noted that the streaker strip 18 and handle 20 that is discarded has not become contaminated by contacting any infected portions of the patient so that the possibility of contaminating operators, or the like, is minimized. Likewise, the remaining portion of the streaker strip 18 and the streaker plate 48 with the inoculating pads 52 thereon, is now stored in the proximal end 19 of the housing 12 so as not to contaminate or infect operators or the area surrounding the apparatus.

The cap 24 is reassembled on the housing 12 and bar 16 which is then incubated for an appropriate period of time at an appropriate temperature. At the conclusion of the incubation period, the cap 24 and the clamps 14 are removed and the identification bar 16 is inspected by the microbiologist, or the like, to analyze and determine the nature of the infections being examined for. The housing 12 with the streaker plate 48 and inoculator pads 52 can now be disposed of. After the identification bar 16 has served its purpose, it can be reassembled with the housing 12 using the clamps 14 and the cap 24 whereupon the entire assembly can be disposed of without exposing the contaminating surfaces to the operator or to the surrounding environment.

INDUSTRIAL APPLICABILITY

The troughs 58, 59, 60, 61 in the identification bar 16 are preloaded by the manufacturer with testing media, one being blood agar containing one unit of bacitracin per milliliter of blood agar in trough 58, a second being ordinary blood agar in trough 59, a third being bile esculin agar in trough 60, and the fourth being mannitol salt agar (6.5%) in trough 61. The bag and plastic cap 24 are removed. With the patient's head held upright for access to the throat, the apparatus 10 is inserted into the mouth to swab the inoculating pads 52 over the infected area or over the site of the inflammation.

The handle 20, streaker strip 18 and pads 52 are then pulled back as the assembly is removed from the patient's mouth. When the handle 20 is back as far as possible, the strip 18 is broken off at the notch 44. The handle 20 and the greater portion of the streaker strip 18 can now be disposed of. These pieces are not contaminated. As the streaker strip 18 was being pulled back, the inoculating pads 52 were drawn across the surfaces of the four testing media in the troughs 58, 59, 60 and 61 in the identification bar 16. The media on the identification bar 16 is now contaminated with the organisms present in the throat. The inoculating pads 52 are now in the full retracted position as is illustrated in FIGS. 4 and 5 and will remain there. The protective cap 24 is replaced on the assembly and the apparatus is incubated at 37° C. for approximately twenty-four hours.

After incubation, the protective cap 24 and clamps 14 are removed and the identification bar 16 can be read or interpreted as follows: (A) Beta-hemolytic colonies on trough 58 and trough 59 with no bile solubility (black precipitate in bile esculin agar) in trough 61 and no growth on mannitol salt in trough 60 indicates Streptococcus organisms other than group A, (B) no Beta-hemolytic colonies on trough 58 but hemolytic colonies on trough 59 with no bile solubility (through trough 61) and no growth on mannitol salt in trough 60 indicates Beta-hemolytic Streptococci group A, (C) Beta-hemolytic colonies on troughs 58 and 59 with bile solubility (black precipitate) in trough 61 with no growth on mannitol salt (trough 60) indicates Enterococcus organisms, (D) Beta-hemolysis on troughs 58 and 59 with no bile solubility in trough 61 with growth on mannitol salt (trough 60) indicate Straphlococcus organisms. The entire apparatus can be discarded after use. However, if it is desired, individual colonies can be cultured from the colonies on the test media on the identification bar 16 for further study.

I claim:

1. In an apparatus for sampling and identifying microorganisms, a housing having an internal elongate cavity; said cavity having an opening through the entire length of one wall of said housing, a streaker strip slidable in said cavity and having an inoculating pad on one end thereof, said inoculating pad projecting beyond one end wall of said housing, an identification bar having at least one open-faced trough formed in one surface thereof, and means for securing said identification bar adjacent the opening through said one lengthwise wall of said housing with said open-faced trough facing said opening, said inoculating pad being drawn over said open-faced trough as said streaker strip is drawn through said housing.

2. In an apparatus as claimed in claim 1 wherein said streaker strip has means for facilitating severing the strip from the inoculating pad when said pad is fully drawn into said housing.

3. In an apparatus as claimed in claim 1 wherein said streaker strip has a handle on the end opposite said inoculating pad, said handle extends outwardly of said housing and is used to draw the strip and pad into the housing and across the open face of the trough.

4. In an apparatus as claimed in claim 1 wherein cap means is provided for covering said inoculating pad and is secured to the distal end of the housing and identification bar.

5. An apparatus for sampling and identifying microorganisms, a housing having an internal elongate cavity; said cavity having an opening through both end walls and through the entire length of one wall of the housing, a strip slidable in said cavity and having an inoculating pad carried by the distal end thereof, said inoculating pad projecting beyond one end wall of said housing, means extending from the other end wall of said housing and connected to said strip for use in drawing said strip and inoculating pad into said housing, an identification bar having at least two open-faced troughs formed in one surface thereof, means for securing said identification bar adjacent the opening through said lengthwise wall of said housing with said open-faced troughs facing said opening in the housing, said inoculating pad being drawn over said open-faced troughs as said strip is drawn through said housing, and means on said strip for facilitating severing the strip from said inoculating pad.

6. An apparatus as claimed in claim 5 wherein cap means are secured to the end of the housing and encloses the inoculating pad.

7. An apparatus as claimed in claim 5 wherein a different testing media is located in each open-faced trough with the surfaces of the media exposed to the inoculating pads as the pads are drawn across the identification bar.

8. An apparatus as claimed in claim 5 wherein said identification bar has four open-faced troughs.

9. An apparatus as claimed in claim 8 wherein one of said troughs contains blood agar, another of said troughs contains blood agar containing one unit of bacitracin per milliliter of blood agar, another of said troughs contains bile esculin agar and the last trough contains mannitol salt agar (6.5%).

10. A method of sampling and identifying pathogenic microorganisms using an apparatus having a housing having an internal elongate cavity,; said cavity having an opening through the entire length of one lengthwise wall with a strip retractable only in a longitudinal direction along the opening in the lengthwise wall and disposed within said housing, a pair of inoculating pads laterally disposed on the distal end of said strip and extending distally of said housing, an identification bar attached to said housing adjacent said lengthwise opening and having a plurality of laterally adjacent pairs of troughs containing media of blood agar, blood agar containing one unit of bacitracin per millimeter of blood agar, bile esculin agar and mannitol salt agar (6.5) therein, said plurality of pairs of troughs being disposed along the length of said identification bar, said apparatus being inserted in a patient's mouth with the inoculating pads being wiped over the infected area, retracting the strip and pads along said lengthwise opening in a longitudinal direction to the housing as the apparatus is removed from the mouth, continuing to retract the strip and the pair of laterally disposed pads to draw the pads across the surface of the plurality of pairs of troughs of media on said bar to inoculate the pairs of troughs of media in sequential order, severing the strip and incubating the apparatus for twenty-four hours, removing the identification bar from the housing and analyzing the colonies grown on the media to identify the microorganisms.

* * * * *